United States Patent [19]

McShane

[11] Patent Number: 4,558,123

[45] Date of Patent: Dec. 10, 1985

[54] 3-EXOMETHYLENE CEPHALOSPORINS

[75] Inventor: Lawrence J. McShane, Indianapolis, Ind.

[73] Assignee: Eli Lilly and Company, Indianapolis, Ind.

[21] Appl. No.: 516,215

[22] Filed: Jul. 22, 1983

[51] Int. Cl.[4] ............... C07D 501/22; A61K 31/545
[52] U.S. Cl. ........................... 544/16; 544/22; 544/28; 544/30
[58] Field of Search ............ 544/16, 26, 27, 22, 544/25, 28, 30, 21; 424/246; 514/200, 209, 202

[56] References Cited

U.S. PATENT DOCUMENTS

| | | | |
|---|---|---|---|
| 3,792,995 | 2/1974 | Ochiai et al. | 260/243 C |
| 3,830,700 | 8/1974 | O'Callagham et al. | 544/22 |
| 3,883,518 | 5/1975 | Ponticello et al. | 260/243 C |
| 3,929,775 | 12/1975 | Ochiai et al. | 260/243 C |
| 4,013,653 | 3/1977 | Wolfe | 260/244 R |
| 4,060,688 | 11/1977 | Chauvette et al. | 544/16 |
| 4,389,524 | 6/1983 | Scartazzini et al. | 544/16 |
| 4,436,596 | 3/1984 | Hall | 204/59 R |

FOREIGN PATENT DOCUMENTS 1326531  8/1973  United Kingdom .
1450718  9/1976  United Kingdom .

OTHER PUBLICATIONS

U.S. application docket X-5900 by Larry McShane entitled "Azetidinone Sulfinic Acids From Cephalosporin Sulfones".

*Primary Examiner*—Nicholas S. Rizzo
*Attorney, Agent, or Firm*—Charles W. Ashbrook; Arthur R. Whale

[57] ABSTRACT

3-Acetoxymethylcephalosporins are converted to 3-exomethylene cephalosporins by reaction with a metal and a bound proton source.

5 Claims, No Drawings

3-EXOMETHYLENE CEPHALOSPORINS

BACKGROUND OF THE INVENTION

Cephalosporins bearing a 3-exomethylene group are valuable intermediates in the synthesis of cephalosporins having antibacterial activity. Chauvette, for example, in U.S. Pat. No. 3,925,372, described the ozonolysis of 3-exomethylenecephams to 3-hydroxy-3-cephems, followed by halogenation of the latter compounds to give 3-halo-3-cephem antibiotics. One 3-chloro-3-cephem is now known commercially as cefaclor.

Several processes are known for the synthesis of 3-exomethylenecephams. Chauvette and Pennington, in *J. Org. Chem.*, 38, 2994 (1973), disclose the reaction of a 3-acetoxy-3-cephem (a cephalosporanic acid derivative) with a sulfur nucleophile such as thiourea to give a 3-thiomethyl-3-cephem derivative, and then reduction of the latter compound with zinc in formic acid and dimethylformamide to give the corresponding 3-exomethylenecepham. Ochiai et al., in U.S. Pat. No. 3,792,995, report an electrolytic reductive cleavage of the 3-acetoxy group of cephalosporanic acid derivatives to give 3-exomethylenecephams. Teijin, in Japanese Pat. No. 51,141889, discloses the preparation of 3-exomethylenecephams from 3-trifluoroacetoxy-3-methylcephams by reaction with a strong acid such as methanesulfonic acid. Kukolja, in U.S. Pat. No. 4,052,387, described the conversion of monocyclic azetidinone-2-sulfinyl chlorides to 3-exomethylenecephams by reaction with a Friedel-Crafts catalyst. Ponticello et al., in U.S. Pat. No. 3,883,518, disclose the reduction with zinc and acetic acid of a 3-carbamoyloxymethyl or 3-acetoxymethyl cephalosporin to give the corresponding 3-exomethylenecepham.

All of the prior art methods for preparing 3-exomethylenecephams suffer in several respects. Those methods that require $C^3$-derivatives other than acetoxy are costly in that additional reaction steps from natural products are required. The methods that require the presence of acids for prolonged periods of time suffer from $\Delta^3$ isomerization. Moreover, yields of 3-exomethylenecephams from prior art processes generally have been low.

An object of this invention is to provide an improved process for preparing 3-exomethylenecephams from 3-acetoxymethyl-3-cephems. The method of this invention differs from the prior art processes in that high yields of 3-exomethylenecephams are realized, and no free acid is permitted in the reaction mixture, thus obviating the risk of substantial undesired side reactions.

SUMMARY OF THE INVENTION

This invention concerns a process for converting 3-acetoxymethyl-3-cephems to 3-exomethylenecephams. The invention is more particularly directed to a method for preparing a 3-exomethylenecepham compound of the formula

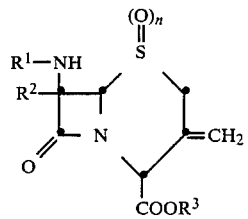

wherein:
$R^1$ is an acyl residue of a carboxylic acid;
$R^2$ is hydrogen, lower alkoxy or lower alkylthio;
$R^3$ is a removable ester forming group; and
n is 1 or 2; comprising reacting a 3-acetoxymethyl cephem of the formula

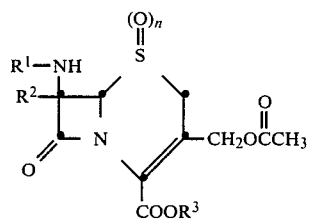

with activated zinc, magnesium, activated magnesium, or amalgamated magnesium, in the presence of a bound proton source in a suitable solvent at a temperature of about $-30°$ C. to about $+30°$ C.

A preferred process comprises employing a starting material a 3-acetoxymethyl-3-cephem-1-oxide, wherein n in the above formulas is 1. Another preferred starting material is a 3-acetoxymethyl-3-cephem-1,1-dioxide wherein n is 2.

A further preferred embodiment employs ammonium chloride as the bound proton source.

Another preferred embodiment employs N,N-dimethylformamide and water (about 10% to about 20% water by volume) as a reaction solvent, particularly when n is 1. A preferred solvent when n is 2 is an alcohol such as ethanol.

The most preferred metal to be employed is activated zinc.

Additionally preferred is a process for preparing a 3-exomethylenecepham defined by the above formula wherein $R^1$ is an acyl residue of a carboxylic acid selected from the group defined by the formulas

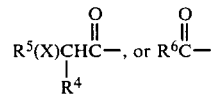

wherein:
$R^4$ is hydrogen, amino, protected amino, hydroxy, protected hydroxy, tetrazolyl, carboxy, or protected carboxy;
$R^5$ is hydrogen, phenyl, substituted phenyl, cyclohexadienyl, or a 5- or 6-membered monocyclic heterocyclic ring containing one or more oxygen, sulfur or nitrogen hetero atoms in the ring, said ring being substituted with hydrogen or amino;
X is oxygen or a direct link, and
$R^6$ is hydrogen, phenyl, substituted phenyl, alkyl, or substituted alkyl.

The process of this invention is conveniently carried out employing 3-acetoxymethyl-3-cephems wherein the side chain defined above by $R^1$ is:

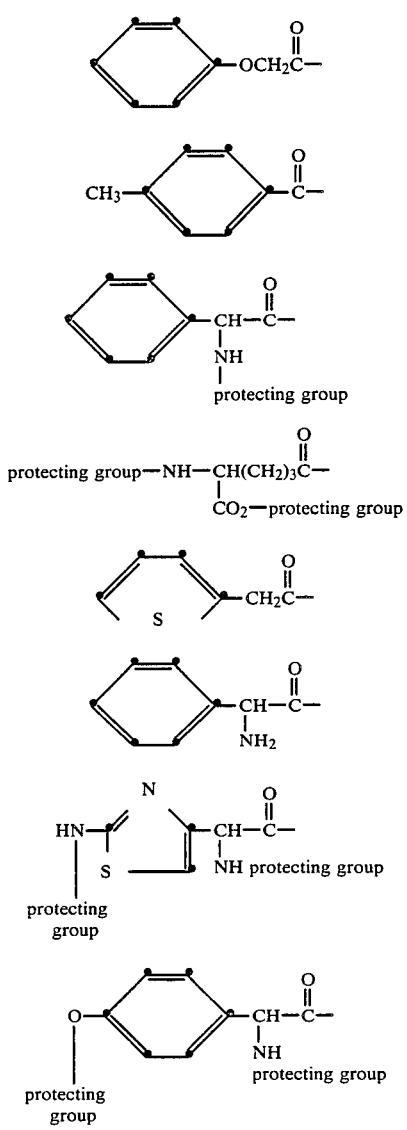

This invention also provides new compounds which are 3-exomethylene cepham sulfones defined by the formula

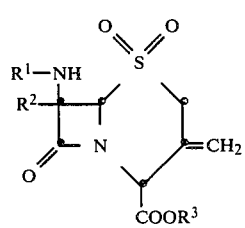

wherein $R^1$, $R^2$ and $R^3$ are as defined above.

DETAILED DESCRIPTION OF THE INVENTION $R^1$ in the above formula defines an acyl residue of a carboxylic acid. Since the process of this invention operates on the acetoxymethyl group attached at the 3-position of a cephalosporanic acid derivative, the particular $R^1$ group attached to the 7-amino group of the cephalosporin is not critical to the process. Numerous and varied acyl residues of carboxylic acids are known in the cephalosporin and penicillin arts, and 3-acetoxymethyl cephalosporins bearing any such acyl residues can be employed in the process of this invention. U.S. Pat. No. 4,052,387 is incorporated herein by reference for its teaching of typical acyl residues employed in the cephalosporin art.

Among the most common acyl residues defined by $R^1$ are groups of the formula

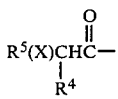

wherein X, $R^4$ and $R^5$ are as defined above. Typical acyl residues so defined include those wherein $R^4$ is hydrogen or amino and $R^5$ is phenyl or substituted phenyl. The term "substituted phenyl" means a phenyl group bearing one or two substituents such as lower alkyl, for example $C_1$–$C_4$ alkyl, amino, hydroxy, or lower alkoxy. When a hydroxy group is present, it generally is desirable to derivatize it with any of the common hydroxy protecting groups in order to facilitate solubility and avoid any unwanted side reactions that might otherwise occur. Common hydroxy protecting groups include formyl, acetyl, diphenylmethyl, 4-methylbenzyl, trimethylsilyl, tert.-butyl, methoxymethyl, and any other readily cleavable hydroxy protecting group commonly employed in cephalosporin and penicillin chemistry.

It is also desirable to derivatize (i.e. protect) any amino groups that might be present in a 3-acetoxymethyl cephalosporin starting material in order to avoid side reactions and to facilitate solubility. Like hydroxy protecting groups, "amino protecting groups" are well known in the cephalosporin and penicillin arts. Typical amino protecting groups include tert.-butoxycarbonyl, benzyloxycarbonyl, 4-methoxybenzyloxycarbonyl, and the like. Protecting groups commonly employed for hydroxy groups, amino groups and carboxylic acid groups are described in more detail by McOmie in "Protective Groups in Organic Chemistry:, Plenum Press, New York, N.Y., 1973, and by Greene in "Protective Groups in Organic Synthesis", John Wiley & Sons, New York, N.Y. 1981.

Exemplary carboxylic acid acyl residues defined by

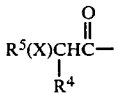

include phenylacetyl, phenoxyacetyl, 4-methylphenylacetyl, 4-tert.-butoxyphenyl acetyl, 3,4-diethylphenylacetyl, 2-furylacetyl, 2-thienylacetyl, 3-thienylacetyl, cyclohexadienylacetyl, 4-tert.-butoxyphenoxyacetyl, α-acetamidophenylacetyl, α-ethoxycarbonylphenylacetyl, and related carboxylic acid acyl residues.

A preferred carboxylic acid acyl residue for use in compounds to be employed in the present process is defined by

Exemplary of these groups are benzoyl, 4-methylbenzoyl, 3-ethylbenzoyl, formyl, acetyl, aminoacetyl, methoxyacetyl, 4-ethylphenylacetyl, butyryl, pentanoyl, 5-aminopentanoyl, 5-carboxypentanoyl, 5-amino-5-carboxypentanoyl, 5-tert.-butylamino-5-diphenylmethylcarboxypentanoyl, and related carboxylic acid aryl residues.

$R^2$ in the above formulas includes lower alkoxy such as methoxy and ethoxy, and lower alkylthio such as methylthio, ethylthio, n-butylthio and the like. The process is preferably carried out with compounds wherein $R^2$ is hydrogen.

As defined above, $R^3$ is a "removable ester forming group". This term means any number of carboxylic acid protecting groups that are readily removed by conventional methods. All such groups are well known in the art, and include groups such as diphenylmethyl, silyl, benzyl, p-methoxyphenyl, phenacyl, tetrahydropyranyl, and the like. A preferred removable ester forming group is diphenylmethyl. U.S. Pat. No. 4,052,387 describes additional removable ester forming groups and is incorporated herein for that teaching.

The process provided by this invention is a method for converting a 3-acetoxymethyl-3-cephem sulfoxide or sulfone to the corresponding 3-exomethylenecepham. The process is carried out by reacting the 3-acetoxymethyl-3-cephem with activated zinc, magnesium, activated magnesium, or analgamated magnesium in the presence of a bound proton source in a mutual solvent at a temperature of about −30° C. to about +30° C. As noted above, any 7-acylamido cephalosporanic acid derivative can be employed as substrate in the process; all that is required is that the cephalosporin be a 3-acetoxymethyl-3-cephem sulfoxide or sulfone derivative.

The terms "activated zinc" and "activated magnesium" mean the respective metal that has substantially no oxide coating. For example, commercially available zinc dust generally is coated with one or more layers of zinc oxide. The zinc oxide coating can be removed, thus providing the activated zinc, by treatment with a mineral acid, for example hydrochloric acid or hydrobromic acid. This is generally accomplished by simply washing the zinc dust prior to use with an aqueous acid solution, for instance 1N hydrochloric acid or the like, and then rinsing the zinc with water or an organic solvent, preferably the solvent that is to be employed in the process of the invention, for example N,N-dimethylformamide or the like. The activated zinc or activated magnesium can be air dried if desired, and then employed directly in the process of the invention. For example, activated zinc can be added to a reaction mixture comprised of the 3-acetoxymethyl-3-cephem substrate and the bound proton source in a suitable reaction solvent. While the exact amount of activated zinc or other metal employed is not critical to the process, an equal weight amount, or more preferably a 1 to 5 weight excess relative to the 3-acetoxymethyl-3-cephem, is desired. As noted above, magnesium, activated magnesium and amalgamated magnesium can also be employed in the present process.

The process of the invention requires the use of a bound proton source. The term "bound proton source" means any agent that is capable of releasing an available proton when in the presence of activated zinc or such other metal and a 3-acetoxymethyl-3-cephem compound. Such bound proton sources will typically include any of the protonic acid addition salts of amines. For example, an amine such as ammonia readily forms acid addition salts with both organic and inorganic protonic acids. Exemplary of such bound proton sources thus formed are ammonium chloride, ammonium bromide, ammonium acetate, ammonium benzoate, ammonium formate, ammonium sulfate, ammonium phosphate, and related ammonium salts. Other amines such as triethylamine, trimethylamine, n-butylamine, glycine, di-n-butylamine, N,N-dimethylcyclohexylamine, methylamine, dimethylamine, aniline, guanidine, and isopropylamine similarly form ammonium and aminium salts by reaction with protonic acids, and thus can be employed to form bound proton sources for use in the present process. Aromatic amines such as pyridine, and non-aromatic cyclic amines such as pyrrolidine also form acid addition salts that can serve as bound proton sources in the present process. All that is required is that a source of protons is available in the reaction mixture to react with the metal and the 3-acetoxymethyl-3-cephem substrate, but that the reaction mixture be substantially free of free acid. In other words, the pH of the reaction mixture should not fall below about 3.0, nor rise above about 8.5. Ideally, the pH of the reaction mixture will be about 4.5 to about 8.0, and more preferably about 5.5 to about 7.5.

Any number of solvents can be employed as suitable mutual reaction solvent in the process of this invention. The solvent selected is preferably one in which the 3-acetoxymethyl-3-cephem substrate is substantially soluble, although this is not a critical requirement of the invention. Solvents most commonly utilized include the polar organic solvents such as N,N-dimethylformamide (DMF), N,N-diethylformamide, dimethylsulfoxide, N-methylformamide, N,N-dimethylacetamide and the like. Less polar organic solvents can also be employed, for example alcohols such as methanol, ethanol and isopropanol, as well as ethers such as tetrahydrofuran, dioxane, methyl ethyl ether, and the like. More than one solvent can be employed in the process if desired, including water. A preferred solvent system employs a mixture of DMF and water in a volume ratio of about 4 to 1. Such solvent systems are espically preferred when a sulfoxide substrate is employed. Alcohol solvents are more preferred when sulfones are employed as substrates.

The process provided by this invention is carried out at a temperature generally below or near room temperature, typically from about −30° C. to about +30° C. Higher reaction temperatures have been found to promote isomerization such that substantial quantities of 3-methyl-3-cephem is produced from the initial 3-exomethylenecepham. This is particularly true in the case of sulfoxide substrate, and lower temperatures are thus preferred when the process is carried out on a sulfoxide.

Because the 3-acetoxymethyl-3-cephem starting material is only partially soluble in some solvents that are employed, it is often desirable to combine the cephalosporin substrate, solvent and bound proton source at a temperature above +10° C., for example at room temperature or higher, thereby aiding solubilization of the cephalosporin substrate. When the substrate is a 3-acetoxymethyl-3-cephem sulfoxide, the reaction mixture is preferably cooled to about −10° C. or below prior to addition of the activated zinc or other metal. The reaction is then carried out at about −20° to about 0° C. once the metal is added. In the case of sulfones, the entire reaction can be conducted at a higher temperature, for instance about room temperature (i.e. 25° C.)

In carrying out the process of the invention, it may be desirable to add to the reaction mixture additional agents that act as buffers or scavengers for any free base (i.e. free amine) that might be present in the reaction mixture as impurity or the like. For example, while DMF is a preferred solvent for the process (especially together with water) commercial DMF often contains dimethylamine as an impurity. Since any free base in the reaction mixture tends to promote formation of 3-methyl-3-cephem products, it is desirable, although not critical, to have present in the reaction mixture an agent that will complex with or otherwise tie up any such free base. Commonly used base scavengers include Lewis acids such as zinc chloride, zinc bromide, ferric chloride, stannic chloride, aluminum chloride and boron trifluoride. A preferred Lewis acid for use in the present process is zinc chloride. Other buffering agents include ethylenediaminetetraacetic acid (EDTA), which is particularly preferred when the process is carried out on a cephalosporin sulfone substrate.

As noted above, the use of a Lewis acid or other buffering agent is not critical to the process. If such agent is employed, it generally is present in about an equal weight amount relative to the 3-acetoxymethyl-3-cephem substrate. Excessive amounts, for instance about a 10 to 50% weight excess, is not detrimental to the progress of the reaction and can be employed if desired.

The conversion of a 3-acetoxymethyl-3-cephem to the corresponding 3-exomethylenecepham according to the process of this invention is generally substantially complete within about two to about forty-eight hours when the reaction is carried out at a temperature of about −30° to about +30° C. Many 3-acetoxymethyl-3-cephem sulfoxide compounds undergo the reaction at a temperature of about 0° to about +10° C. within about two to about five hours, and the 3-exomethylenecepham can be isolated after such time. In a preferred embodiment, the sulfoxides are reacted with a metal and a bound proton source at a temperature of about −20° C. to about +10° C., and at such temperature the reaction generally is substantially complete after about two to about twenty-four hours. The 3-acetoxy-3-cephem sulfone substrates undergo the reaction more quickly than the sulfoxides, and the process is generally substantially complete within about fifteen minutes to about two hours when carried out at room temperature. Formation of 3-methyl-3-cephems appears to occur less with sulfones than with sulfoxides.

Upon completion of the process, the 3-exomethylenecepham product is readily isolated when desired by simply filtering the reaction mixture to remove the metal and any other insoluable material, and then extracting the product from the filtrate. For example, the filtrate can be concentrated by evaporation of highly volatile solvents, and then diluted with water and extracted with a water immiscible organic solvent such as ethyl acetate, dichloromethane, chloroform or the like. Removal of the solvent from the combined extracts by evaporation under reduced pressure affords the 3-exomethylenecepham product. The product can be purified, thus removing any 3-methyl-3-cephem or other impurities that might have been produced, by standard procedures including chromatography and crystallization from solvents such as methanol, isopropanol, benzene and the like.

As pointed out above, the 3-exomethylenecephams produced by the process of this invention are useful as intermediates in the synthesis of cephalosporins having antibacterial activity. The 3-exomethylenecepham-1-oxides are especially useful as intermediates, and a preferred embodiment of this invention is therefore a process for converting 3-acetoxymethyl-3-cephem sulfoxides to 3-exomethylenecepham sulfoxides. The 3-exomethylenecepham sulfoxides are of particular value in the synthesis of 3-hydroxy cephalosporins, which are readily converted to 3-halo cephalosporins, all by known methods. For example, ozonolysis of a 3-exomethylenecepham sulfoxide, derived from an appropriately protected cephalosporin C derivative, affords the corresponding 3-hydroxycepham sulfoxide, which when reacted with a reducing agent is converted to the corresponding 3-hydroxycepham sulfide. Reaction of the latter compound with a halogenating agent such as phosphorus chloride effects halogenation at the 3-position to provide, for example, a 3-chloro-3-cephem sulfide. Removal of any protecting groups or routine side chain cleavage and reacylation then gives a cephalosporin antibiotic such as cefaclor. Such reactions are described in more detail in U.S. Pat. No. 3,925,372.

The 3-exomethylene sulfones prepared by the process of this invention are useful as intermediates in the synthesis of 1-oxadethiacephalosporin antibiotics. For example, such compounds are conveniently converted to azetidinone sulfinic acid by reaction with zinc, and the sulfinic acids are subsequently converted to chloroazeidinones and oxazolines which are useful in the synthesis of 1-oxadethiacephalosporins by the methods described by Tsuji et al. in U.S. Pat. No. 4,220,766, by Narisada et al. in U.S. Pat. No. 4,323,567, and by the methods of U.S. Pat. Nos. 4,138,486, 4,013,653, and 4,159,894.

The process of this invention is more fully described by the following detailed examples.

EXAMPLE 1

Activation of zinc dust

About 5 gms. of zinc metal dust were placed on a sintered glass funnel and triturated with 20 ml. of 2.5 percent (v/v) aqueous hydrochloric acid. The aqueous acid was removed as filtrate, and fresh acid solution was added. The aqueous acid was again removed as filtrate, and the zinc dust was triturated several times with N,N-dimethylformamide.

EXAMPLE 2

Diphenylmethyl 7-β-(4-methylphenylcarboxamido)-3-exomethylenecepham-1-oxide-4-carboxylate A solution of 1.14 gm. (2 mmoles) of diphenylmethyl 7-β-(4-methylphenylcarboxamido)-3-acetoxymethyl-3-cephem-1-oxide-4-carboxylate in 25 ml. of N,N-dimethylformamide (DMF) and 5 ml. of water containing 2.0 gm. of ammonium chloride was stirred under a nitrogen atmosphere and cooled to 0°–5° C. in an ice/water bath. Two and one-half grams of activated zinc were added to the reaction mixture in one portion, and the slurry was vigorously stirred for 5 hours at 0°–5° C. The zinc was then removed by filtration and washed with 50 ml.

of ethyl acetate. The filtrate was then washed with 50 ml. of water and 50 ml. of five percent (v/v) aqueous hydrochloric acid, and finally with saturated aqueous sodium chloride. The organic layer was treated with charcoal and dried over magnesium sulfate. Removal of the drying agent by filtration and evaporation of the filtrate under reduced pressure afforded 1.0 gm. of a white foam. The foam was triturated with 10 ml. of methanol and then chilled at 0° C. for twelve hours to provide 610 mg. of diphenylmethyl 7-β-(4-methylphenylcarboxamido)-3-exomethylenecepham-1-oxide-4-carboxylate. Yield 59.2%.

NMR (CDCl$_3$) demonstrated the product to be comprised of approximately 94% pure 3-exomethylenecepham and about 6% 3-methyl-3-cephem isomer (δ 4.9, doublet, exomethylene; δ 2.1, singlet, 3-methyl). High pressure liquid chromatography confirmed the product to be composed of about 94% pure 3-exomethylenecepham.

EXAMPLE 3

The reaction of Example 2 was repeated by dissolving 1.14 gm. of diphenylmethyl 7-β-(4-methylphenylcarboxamido)-3-acetoxymethyl-3-cephem-1-oxide-4-carboxylate in 25 ml. of N-methylformamide at 25° C. under nitrogen. Two grams of ammonium chloride were added to the reaction mixture, and then it was cooled to 4° C. in an ice/water bath and stirred. Two and one-half grams of activated zinc were added to the reaction mixture in one portion, and stirring was continued at 4° C. for 3½ hours. The progress of the reaction was monitored by thin layer chromatography.

Upon completion of the reaction, the zinc was removed by filtration and washed with 25 ml. of fresh methylformamide. The filtrate was diluted with 100 ml. of water and 100 ml. of ethyl acetate. Two milliliters of acetic acid were added to break the emulsion that had formed, and then the ethyl acetate layer was separated. The aqueous layer was washed with fresh ethyl acetate, and the organic layers were combined, washed with aqueous sodium chloride, treated with charcoal and then dried. Removal of the solvent by evaporation provided a foam, which upon crystallization from 10 ml. of methanol gave 560 mg. of diphenylmethyl 7-β-(4-methylphenylcarboxamido)-3-exomethylenecepham-1-oxide-4-carboxylate. Yield 55%.

EXAMPLE 4

To a stirred solution of 5.72 gm. (10 mmoles) of diphenylmethyl 7-β-(4-methylphenylcarboxamido)-3-acetoxymethyl-3-cephem-1-oxide-4-carboxylate in 175 ml. of DMF and 25 ml. of water were added in one portion 10.0 gm. of ammonium chloride. The reaction mixture was stirred under nitrogen and cooled to −10° C. in an ethanol/ice bath. Twelve and one-half grams of activated zinc were added in one portion to the cold stirred reaction mixture. The reaction mixture was stirred vigorously for 9½ hours at a temperature maintained at −10° to −5° C. The reaction mixture was stored at −20° C. for twelve hours, and stirred for an additional 2 hours at −10° C. The solids were removed by filtration and washed with 250 ml. of ethyl acetate. The filtrate was washed with 375 ml. of water and 125 ml. of 5% hydrochloric acid, followed by an additional 500 ml. of water and then 100 ml. of saturated aqueous sodium chloride. The organic layer was washed again with 300 ml. of water, 200 ml. of saturated brine, and finally with another 100 ml. portion of fresh water. The organic layer was dried and the solvent was removed by evaporation under reduced pressure to provide a white solid. The solid was crystallized from 30 ml. of methanol to give 3.15 gm. of diphenylmethyl 7-β-(4-methylphenylcarboxamido)-3-exomethylenecepham-1-oxide-4-carboxylate. Yield 61.3%.

NMR (CDCl$_3$) demonstrated that the product was 94% 3-exomethylene and 6% 3-cephem isomer. This isomer ratio was confirmed by high pressure liquid chromatography.

EXAMPLE 5

The product from Example 4 was further purified by suspending 2.0 gm. of the mixture in 25 ml. of isopropyl alcohol and heating the mixture on a steam bath. Dichloromethane was then added until all of the solids had dissolved. The solution was heated until all of the dichloromethane was evaporated. As the solution cooled, a white crystalline product formed to give 1.6 g. of pure diphenylmethyl 7-β-(4-methylphenylcarboxamido)-3-exomethylenecepham-1-oxide-4-carboxylate.

Analysis calculated for $C_{28}H_{25}N_2O_4S$ Theory: C, 67.69; H, 5.09; N, 5.44; O, 15.55; S, 6.23. Found: C, 67.80; H, 5.14; N, 5.18; O, 15.79; S, 6.16.

IR (CHCl$_3$) 1780 cm$^{-1}$ β-lactam carbonyl; 1740 cm$^{-1}$ ester carbonyl; 1670 cm$^{-1}$ amide carbonyl; NMR (CDCl$_3$) δ 3.57 (quartet, 2H, C$^2$); δ 5.43, δ 5.78 (2 singlets, 2H, 3-exomethylene) δ 5.33 (singlet, 1H, C$^4$); δ 4.89 (doublet, 1H, C$^6$); δ 6.13 (quartet, 1H, C$^7$); δ 2.36 (singlet, 3H, CH$_3$); δ 6.83 (singlet, 1H, diphenylmethyl CH) δ 7.1–7.7 (multiplet, 15H, aromatic and NH).

EXAMPLE 6

Diphenylmethyl 7-β-phenoxyacetamido-3-exomethylenecepham-1-oxide-4-carboxylate

To a cold (0° C.) stirred solution of 2.35 gm. (4 mmoles) of diphenylmethyl 7-β-phenoxyacetamido-3-exomethylenecepham-1-oxide-4-carboxylate in 50 ml. of DMF containing 10 ml. of water were added in individual portions 2.7 gm. (2 mmoles) of zinc chloride, 4.0 gm. of ammonium chloride, and finally 5.0 gm. of activated zinc dust. The reaction mixture was stirred at 0°–5° C. for 36 hours, and the solids were then removed by filtration and washed with ethyl acetate. The filtrate was extracted into 200 ml. of ethyl acetate, and the organic phase was washed three times with 250 ml. of water containing a small amount of 6N hydrochloric acid to break up any emulsion. The organic layer was washed with brine and dried, and the solvent was removed by evaporation under reduced pressure to give a white foam. The foam was triturated with 25 ml. of methanol and then air dried to afford 1.65 g. of 95% pure diphenylmethyl 7-β-phenoxyacetamido-3-exomethylenecepham-1-oxide-4-carboxylate (about 5% of 3-cephem was present).

NMR (CDCl$_3$) δ 3.50 (quartet, 2H, C$^2$); δ 5.43, 5.77 (2 singlets, 3-exomethylene); δ 5.30 (singlet, 1H, C$^4$); δ 4.80 (doublet, 1H, C$^6$); δ 5.95 (quartet, 1H, C$^7$); δ 4.50 (singlet, 2H,

δ 6.84–7.50 (multiplet, 16H, aromatic and diphenylmethyl); δ 8.08 (doublet, 1H, NH).

EXAMPLE 7

Diphenylmethyl 7-β-phenylacetamido-3-exomethylenecepham-1-oxide-4-carboxylate

A solution comprised of 2.28 gm. (4 mmoles) of diphenylmethyl 7-β-phenylacetamido-3-acetoxymethyl-3-cephem-1-oxide-4-carboxylate in 75 ml. of DMF and 10 ml. of water was stirred and cooled to 0°–5° C. in an ice/water bath. To the cold reaction mixture were added 2.7 gm. of zinc chloride, 4.0 gm. of ammonium chloride and 5.0 gm. of activated zinc dust. The reaction mixture was stirred at 0°–5° C. for 6 hours, and then stored at 0° C. for 6 days. The solids were removed by filtration and washed several times with ethyl acetate. The ethyl acetate layer was separated from the filtrate, and the aqueous DMF layer was extracted several times with fresh ethyl acetate. The ethyl acetate extracts and washings were combined, washed with brine and dried. Removal of the solvent by evaporation afforded 1.27 gm. of a solid product that was shown to be about 90% diphenylmethyl 7-β-phenylacetamido-3-exomethylenecepham-1-oxide-4-carboxylate and about 10% diphenylmethyl 7-β-phenylacetamido-3-methyl-3-cephem-1-oxide-4-carboxylate. The mixture was separated on high pressure liquid chromatography to afford 540 mg. of pure 3-exomethylenecepham.

NMR (CDCl$_3$) δ 3.42 (quartet, 2H, C$^2$) δ 5.33, 5.67 (2 singlets; 2H, 3-exomethylene; δ 5.23 (singlet, 1H, C$^4$); δ 4.70 (doublet, 1H, C$^6$); δ 5.84 (quartet, 1H, C$^7$); δ 3.52 (singlet, 2H,

δ 6.77 (singlet, 1H, diphenylmethyl CH); δ 7.23 (multiplet, 16H, aromatic and NH).

EXAMPLE 8

Diphenylmethyl 7-β-(4-methylphenylcarboxamido)-3-exomethylenecepham-1-oxide-4-carboxylate A solution of 2.7 gm. (20 mmoles) of zinc chloride in 50 ml. of DMF containing 10 ml. of water was stirred under nitrogen and cooled to about 3° C. in an ice/water bath. Four grams of ammonium chloride were added in one portion to the cold reaction mixture, followed by the addition in one portion of 2.28 gm. (4 mmoles) of diphenylmethyl 7-β-(4-methylphenylcarboxamido)-3-acetoxymethyl-3-cephem-1-oxide-4-carboxylate. To the cold stirred reaction mixture were then added 5.0 gm. of zinc dust, activated as described in Example 1. The reaction mixture was stirred at about 3° C. for 6 hours, and then was stirred at 0° C. for 48 hours. Thin layer chromatographic analysis demonstrated that the reaction was complete and that the product was substantially a single compound.

The reaction mixture was filtered and the solids were washed with 200 ml. of ethyl acetate. The filtrate was diluted with 250 ml. of water, and the pH of the mixture was adjusted to 7.0 by the addition of dilute hydrochloric acid. The organic layer was separated, and the aqueous layer was extracted several times with fresh ethyl acetate. The ethyl acetate portions were combined, washed with brine and dried. Removal of the solvent by evaporation under reduced pressure provided 1.9 gm. of a white solid. High pressure liquid chromatography demonstrated that the product was about 92% pure 3-exomethylenecepham. The product was crystallized from 12.5 ml. of methanol to give 1.28 gm. of diphenylmethyl 7-β-(4-methylphenylcarboxamido)-3-exomethylenecepham-1-oxide-4-carboxylate. Yield of pure 3-exomethylenecepham was 61%.

EXAMPLE 9

Diphenylmethyl 7-β-[α-(tert.-butoxycarbonylamino)phenylacetamido]-3-exomethylenecepham-1-oxide-4-carboxylate To a cold (0°–5° C.) stirred solution of 2.75 gm. (4 mmoles) of diphenylmethyl 7-β-[α-(tert.-butoxycarbonylamino)phenylacetamido]-3-acetoxymethyl-3-cephem-1-oxide-4-carboxylate in 50 ml. of DMF and 10 ml. of water were added 2.7 gm. of zinc chloride, 4.0 gm. of ammonium chloride, and finally 5.0 gm. of zinc dust, activated according to the procedure of Example 1. The reaction mixture was stirred at 0°–5° C. for 6 hours, and then was stored at 0° C. for 12 hours. The reaction mixture was filtered and the solids were washed with ethyl acetate. The filtrate was extracted several times with fresh ethyl acetate. The extracts were combined, washed with water and brine, and dried. Removal of the solvent by evaporation under reduced pressure provided an oil. The oil was crystallized from 25 ml. of methanol to provide 1.70 gm. of about 90% pure diphenylmethyl 7-β-[α-(tert.-butoxycarbonylamino)-phenylacetamido]-3-exomethylene-cepham-1-oxide-4-carboxylate. The product was further purified by high pressure liquid chromatography to give 100% pure 3-exomethylene product.

NMR (DMSOd$_6$); δ 3.80 (quartet, 2H, C$^2$); δ 5.23–5.94 (multiplet, 5H, exomethylene, C$^4$, C$^7$, acetamido methine); δ 5.08 (doublet, 1H, C$^6$); δ 1.43 (singlet, 9H, tert.-butyl); δ 6.92 (singlet, 1H, diphenylmethylmethine); δ 7.43 (broad singlet, 15H, aromatic); δ 8.35 (doublet, 1H, NH).

EXAMPLE 10

Following the general procedure of Example 9, 5.4 gm. (40 mmoles) of zinc chloride were dissolved in 100 ml. of DMF at room temperature under nitrogen (causing a slight exothermic reaction). The solution was stirred and cooled to 0°–5° C. in an ice/water bath. To the cold stirred solution were added 5.5 gm. (8 mmoles) of diphenylmethyl 7-β-[α-(tert.-butoxycarbonylamino)-phenylacetamido]-3-acetoxymethyl-3-cephem-1-oxide-4-carboxylate, 10 ml. of water, 8.0 gm. of ammonium chloride and 10 gm. of activated zinc dust (the zinc was activated by washing three times with 3N hydrochloric acid followed by washing three times with water). The reaction mixture was stirred under nitrogen at 0°–5° C. for 6 hours, and then was stored at −10° C. for twelve hours. The reaction mixture was warmed to 0°–5° C. and stirred at that temperature for an additional 10 hours, and then again stored at −10° C. for twelve hours. Thin layer chromatographic analysis (1:1 v/v ethyl acetate-toluene) demonstrated that the product was greater than 90% diphenylmethyl 7-β-[α-(tert.-butoxycarbonylamino)phenylacetamido]-3-exomethylenecepham-1-oxide-4-carboxylate, with a small amount of 3-cephem isomer.

The reaction mixture was filtered and the filtrate was partitioned between ethyl acetate and water. The organic layer was separated, washed with water and brine, dried, and the solvent was removed by evaporation to give a white foam. The foam was triturated with isopropyl alcohol to afford 4.1 gms. of about 90% pure diphenylmethyl 7-β-[α-(tert.-butoxycarbonylamino)-phenylacetamido]-3-exomethylenecepham-1-oxide-4-carboxylate. Yield 81%.

EXAMPLE 11

Diphenylmethyl 7-β-[(5-heptanamido-5-diphenylmethoxycarbonyl)-valeramido]-3-exomethylenecepham-1-oxide-4-carboxylate A solution of 2.7 gm. (20 mmoles) of zinc chloride in 100 ml. of DMF and 10 ml. of water was stirred under nitrogen and cooled to 0°–5° C. in an ice/water bath. Four grams of ammonium chloride were added to the stirred solution, and stirring was continued for 10 minutes, and then 3.5 gm. (4 mmoles) of diphenylmethyl 7-β-[(5-heptanamido-5-diphenylmethoxycarbonyl)-valeramido]-3-acetoxymethyl-3-cephem-1-oxide-4-carboxylate were added in one portion. With continued stirring, 5.0 gms. of activated zinc (activated as in Example 1) were added to the reaction mixture in one portion, and the mixture was stirred for 8 hours at 0°–5° C. Thin layer chromatographic analysis demonstrated that the reaction was incomplete. The mixture was stored at −20° C. for twelve hours, and then stirred at 0°–5° C. for an additional 8 hours. The solids were removed from the reaction mixture by filtration (using hi-flo filter aid) and the filtrate was diluted with ethyl acetate and water. The ethyl acetate layer was separated, washed with water and brine, dried, and the solvent was removed by evaporation under reduced pressure to afford 2.8 gms. of the product as an oil. The oil was crystallized from diethyl ether to give 2.8 gms. of about 80% diphenylmethyl 7-β-[(5-heptanamido-5-diphenylmethoxycarbonyl)valeramido]-3-exomethylenecepham-1-oxide-4-carboxylate and about 20% of the 3-methyl-3-cephem isomer. Yield of 3-exomethylenecepham was shown to be about 68%.

NMR (CDCl$_3$): δ 3.45 (quartet, 2H, C$^2$); δ 5.40, 5.74 (2 singlets, 2H, exomethylene); δ 5.32 (singlet, 1H, C$^4$); δ 4.75 (doublet, 1H, C$^6$); δ 5.84 (quartet, 1H, C$^7$); δ 6.84 (2 singlets, 2H, diphenylmethyl methines); δ 0.80–2.40 (multiplet, 19H, aliphatic); δ 7.10–7.50 (broad singlet, 20H, aromatic); δ 4.67 (multiplet, 1H, methine).

EXAMPLE 12

Diphenylmethyl 7-β-formamido-3-exomethylenecepham-1-oxide-4-carboxylate

To a cold (0°–5° C.) stirred solution of 1.35 gm. of zinc chloride and 2.0 gm. ammonium chloride in 25 ml. of DMF and 5 ml. of water were added in one portion 970 mg. (2 mmoles) of diphenylmethyl 7-β-formamido-3-acetoxymethyl-3-cephem-1-oxide-4-carboxylate. The reaction mixture was stirred vigorously at 0°–5° C. under nitrogen while 2.5 mgs. of activated zinc were added in one portion. Stirring was continued for 5 hours, and then the mixture was stored at −10° C. for twelve hours. The reaction mixture was then filtered, and the filtrate was added to ethyl acetate and water. The ethyl acetate layer was separated, washed with water and brine, dried, and the solvent was removed by evaporation under reduced pressure to give 400 mg. of 85% pure diphenylmethyl 7-β-formamido-3-exomethylenecepham-1-oxide-4-carboxylate. Overall yield of 3-exomethylene about 58%.

NMR (CDCl$_3$): δ 3.53 (quartet, 2H, C$^2$) δ 5.43, 5.77 (2 singlets, 2H, exomethylene); δ 5.33 (singlet, 1H, c$^4$); δ 4.84 (doublet, 1H, C$^6$); δ 5.95 (quartet, 1H, C$^7$); δ 8.17 (singlet, 1H, formyl H); δ 6.84 (singlet, 1H, diphenylmethyl H); δ 7.00–7.50 (singlet, 11H, aromatic and NH).

EXAMPLE 13

Diphenylmethyl 7-α-(4-methylphenylcarboxamido)-3-exomethylenecepham-1,1-dioxide-4-carboxylate To a stirred solution of 294 mg. (0.5 mmole) of diphenylmethyl 7-α-(4-methylphenylcarboxamido)-3-acetoxymethyl-3-cephem-1,1-dioxide-4-carboxylate in 25 ml. of ethanol were added in one portion 500 mg. of ammonium chloride, followed by the addition of 750 mg. of activated zinc (zinc washed twice with 20 ml. portions of 2.5% aqueous hydrochloric acid and several times with ethanol). The reaction mixture was stirred vigorously for 2 hours at room temperature under nitrogen. Thin layer chromatographic analysis demonstrated that the reaction mixture contained predominantly 3-exomethylenecepham product. The zinc was removed by filtration and the ethanol was removed from the filtrate by evaporation to give a product that was about 6 parts diphenylmethyl 7-α-(4-methylphenylcarboxamido)-3-exomethylenecepham-1,1-dioxide-4-carboxylate and about 4 parts of the 3-methyl-3-cephem isomer.

EXAMPLE 14

Diphenylmethyl 7-β-(4-methylphenylcarboxamido)-3-exomethylenecepham-1,1-dioxide-4-carboxylate To a stirred suspension of 2.35 gms. (4 mmoles) of diphenylmethyl 7-β-(4-methylphenylcarboxamido)-3-acetoxymethyl-3-cephem-1,1-dioxide-4-carboxylate in 100 ml. of ethanol were added in one portion 4.0 gms. of ammonium chloride, followed by the addition of 5.0 gms. of activated zinc dust. The reaction mixture was stirred at room temperature under nitrogen for one hour. The solids were then removed by filtration and the solvent was removed from the filtrate by evaporation under reduced pressure to give a white solid. The solid was dissolved in 50 ml. of ethyl acetate, washed twice with 50 ml. portions of water, dried, and the solvent was removed to afford a white foam. The foam was dissolved in warm methanol, and upon cooling, crystalline product formed and was collected by filtration. High performance liquid chromatography demonstrated that the product was 90% diphenyl 7-β-(4-methylphenylcarboxamido)-3-exomethylenecepham-1,1-dioxide-4-carboxylate, and 10% 3-methyl-3-cephem isomer. IR (CHCl$_3$) 1797, 1745, 1680, 1336 cm$^{-1}$.

Analysis calc. for $C_{29}H_{26}N_2O_6S$ Theory: C, 65.65; H, 4.94; N, 5.28; O, 18.09; S, 6.04. Found: C, 65.49; H, 4.99; N, 5.19; O, 17.91; S, 6.12.

NMR (CDCl$_3$): δ 3.67 (singlet, 2H, C$^2$); δ 5.36, 5.46 (2 singlets, 2H, exomethylene); δ 5.36 (singlet, 1H, C$^4$); δ 5.14 (doublet, 1H, C$^6$); δ 6.23 (doublet of doublets, 1H, C$^7$); δ 2.28 (singlet, 3H, methyl); δ 6.80 (singlet, 1H, diphenylmethyl methine); δ 7.00–7.87 (multiplet, 5H, aromatic and NH); δ 1.92 (singlet for 10% 3-methyl).

EXAMPLE 15

Diphenylmethyl
7-β-(4-methylphenylcarboxamido)-3-exomethylenecepham-1,1-dioxide-4-carboxylate A solution of 1.18 gm. (2 mmoles) of diphenylmethyl 7-β-(4-methylphenylcarboxamido)-3-acetoxymethyl-3-cephem-1,1-dioxide-4-carboxylate in 50 ml. of tetrahydrofuran was stirred at room temperature under nitrogen while 2.0 gms. of ammonium chloride were added in one portion, followed by the addition of 2.5 gms. of activated zinc. The reaction mixture was stirred for 48 hours at room temperature, and then filtered. The filtrate was concentrated to a solid by evaporation of the solvent. The solid was dissolved in dichloromethane, filtered, and the solvent was removed by evaporation to give a foam that, when crystallized from 25 ml. of methanol, provided 700 mg. of diphenylmethyl 7-β-(4-methylphenylcarboxamido)-3-exomethylenecepham-1,1-dioxide-4-carboxylate. This product was shown to contain about 10% of the 3-methyl-3-cephem isomer.

EXAMPLE 16

Several experiments were carried out to determine the effect of the particular bound proton source upon the reaction. Diphenylmethyl 7-α-(4-methylphenylcarboxamido)-3-exomethylenecepham-1,1-dioxide-4-carboxylate was prepared from the corresponding 3-acetoxymethyl-3-cephem by reaction with activated zinc and a bound proton source. The reactions were carried out in dimethylformamide and water (80:20 v/v), and ethylenediaminetetraacetic acid was employed to maintain the pH at about 5 to 6. The reaction mixtures were analyzed by high pressure liquid chromatography to determine the percent concentration of the desired 3-exomethylene product, the 3-methyl-3-cephem compound, and starting material. The results of several studies are presented in the following table.

| | Percentage of: | | |
|---|---|---|---|
| Bound Proton Source | 3-exo-methylene | 3-methyl-3-cephem | 3-acetoxy-methyl-3-cephem |
| methylamine hydrochloride | 83.2 | 12.4 | 2.0 |
| dimethylamine hydrochloride | 87.7 | 10.6 | 0.2 |
| trimethylamine hydrochloride | 35.1 | 62.6 | — |
| diethylamine hydrochloride | 62.7 | 11.3 | 6.0 |
| di-n-butylamine hydrochloride | 74.8 | 20.9 | 1.0 |
| pyridine hydrochloride | 63.0 | 35.2 | 0.3 |
| aniline hydrochloride | 43.0 | 16.4 | 39.1 |
| semicarbazide hydrochloride | 82.6 | 16.4 | 0.3 |
| hydroxylamine hydrochloride | 51.7 | 11.5 | 34.2 |
| quanidine hydrochloride | 88.6 | 10.5 | 0.4 |
| glycine hydrochloride | 42.2 | 5.0 | 52.5 |
| n-butylamine hydrochloride | 36.5 | 27.7 | 33.8 |
| n-butylamino hydrochloride (excess) | 77.1 | 21.4 | — |
| aqueous ammonium chloride and acetic acid | 85.0 | 14.5 | — |

EXAMPLE 17

A series of reactions similar to those of Example 16 were carried out to determine the effect of solvent upon the reaction. The bound proton source employed in each reaction was ammonium chloride.

| | Percentage of: | | |
|---|---|---|---|
| Solvent | 3-exo-3-methylene | 3-methyl-3-cephem | 3-acetoxy-methyl-3-cephem |
| DMF—H₂O 80:20 | 90.3 | 7.8 | 0.9 |
| DMF—H₂O 60:40 | 54.0 | 4.4 | 41.2 |
| DMF—NMF—H₂O 60:20:20 | 91.8 | 7.2 | 0.6 |
| DMF—NMF—H₂O 40:40:20 | 91.8 | 7.8 | — |
| DMF—NMF—H₂O—CH₃OH 20:40:20:20 | 81.0 | 9.3 | 6.8 |
| DMF—CH₃OH 70:30 | 40.1 | 19.2 | 2.8 |
| DMSO—H₂O 60:40 | 49.8 | 5.2 | 44.4 |
| DMSO—CH₃OH 50:50 | 60.6 | 21.7 | 7.1 |
| F—CH₃OH 50:50 | 58.5 | 7.6 | 28.8 |

(DMF = N,N—dimethylformamide; NMF = N—methyl-formamide; F = formamide)

EXAMPLE 18

A series of reactions similar to those of Example 16 were carried out to determine the effect of various metals upon the reaction. In each reaction, DMF-water 80:20 was employed as solvent, ammonium chloride was the bound proton source, and EDTA was employed to control the pH. The results are presented in the following table.

| | Percentage of: | | |
|---|---|---|---|
| Metal | 3-exo-methylene | 3-methyl-3-cephem | 3-acetoxy-methyl-3-cephem |
| Zn (HCl activated) | 90.3 | 7.8 | 0.9 |
| Mg | 92.1 | 6.0 | 1.2 |
| Mg (HCl activated) | 83.9 | 14.7 | 0.6 |
| Mg/Hg | 78.9 | 13.7 | 7.1 |

The studies carried out as described in Examples 16–18 establish ammonium chloride as a preferred bound proton source, N,N-dimethylformamide and water as a preferred reaction solvent, and activated zinc as a preferred metal.

EXAMPLE 19

Preparation of
7-β-[2-amino-2-(4-hydroxyphenyl)acetamido]-3-chloro-3-cephem-4-carboxylate from 7-ACA (A) To a stirred cold (5°–10° C.) solution of 64.26 kg. of 7-aminocephalosporanic acid (7-ACA) in 148 liters of water and 117 liters of acetone were added dropwise 18.9 kg. of sodium carbonate in 62 liters of water. The reaction mixture was stirred at 5°–10° C. until all 7-ACA had dissolved. To the cold reaction mixture was added dropwise over one hour a solution of 11.73 liters of 4-methyl benzoyl chloride in 55 liters of acetone. The reaction mixture was stirred at 5°–10° C. for thirty minutes following complete addition, and then heated to 35° C. The acetone was removed from the reaction mixture by evaporation under reduced pressure, and then the pH was adjusted to 7.0 by the addition of conc. hydrochloric acid. The aqueous layer was washed with ethyl acetate, and then diluted with additional hydrochloric acid to pH 2.0. The precipitate which formed was collected by filtration and washed with a mixture of ethyl acetate and water. The precipitate was air dried at 35° C. and identified as 26.10 kg. of 7-β-(4-methylphenylcarboxamido)-3-acetoxymethyl-3-cephem-4-carboxylic acid.

(B) To a stirred cold (0°-5° C.) solution of 36.0 kg. of 7-β-(4-methylphenylcarboxamido)-3-acetoxymethyl-3-cephem-4-carboxylic acid (prepared as described in A) in 460 liters of acetone and 46 liters of water were added dropwise over forty-five minutes 16.1 liters of peracetic acid. The reaction mixture was stirred for twelve hours at 0°-5° C. A solution of 30.7 kg. of benzophenone hydrazone in 140 liters of acetone was added portion-wise over thirty minutes to the cold stirred reaction mixture. Following complete addition, the reaction mixture was stirred at 0°-5° C. for an additional thirty minutes, and then warmed to 25° C. and stirred for twelve hours. The reaction mixture was then cooled to 17°-20° C. and stirred while 9.2 liters of trimethyl phosphite were added dropwise over one hour. The acetone solvent was removed from the reaction mixture by evaporation under reduced pressure, and then 440 liters of isopropyl alcohol were added to the mixture, and the mixture was cooled to 0°-5° C. for sixteen hours. The precipitated solid was collected by filtration and washed with fresh isopropyl alcohol to give 41.65 kg. of diphenylmethyl 7-β-(4-methylphenylcarboxamido)-3-acetoxymethyl-3-cephem-1-oxide-4-carboxylate.

(C) To a cold (−8° C.) stirred (under nitrogen) solution of 20.6 kg. of diphenylmethyl 7-β-(4-methylphenylcarboxamido)-3-acetoxymethyl-3-cephem-1-oxide-4-carboxylate in 630 liters of DMF and 90 liters of water containing 36 kg. of ammonium chloride were added 45 kg. of activated zinc dust. The reaction mixture was stirred for twelve hours at about −8° C. and then filtered. The solids were washed with ethyl acetate, and the filtrate was extracted several times with ethyl acetate. The extracts and washings were combined, washed with water and brine, dried, and the solvent was removed by evaporation under reduced pressure to provide a solid. The solid was crystallized from methanol to give 9.94 kg. of diphenylmethyl 7-β-(4-methylphenylcarboxamido)-3-exomethylenecepham-1-oxide-4-carboxylate.

(D) A solution of 8.0 kg. of diphenylmethyl 7-β-(4-methylphenylcarboxamido)-3-exomethylenecepham-1-oxide-4-carboxylate in 156 liters of dichloromethane was cooled to −70° C. and stirred while ozone gas was bubbled into the solution for fourteen hours. With continued stirring at −70° C., the reaction mixture was diluted by the dropwise addition over fifteen minutes of a solution of 4.5 liters of triphenyl phosphite in 4.5 liters of dichloromethane. The reaction mixture was then concentrated to a volume of 60 liters, whereupon 73 liters of DMF were added. The reaction mixture was stirred at 30° C. for five minutes, and then the remainder of dichloromethane was removed by evaporation, maintaining the temperature at 10°-15° C. The reaction mixture was next cooled to −43° C. and stirred while 3.4 liters of phosphorous trichloride were added in portions over ten minutes. The reaction mixture was warmed to −26° C., and was stirred at that temperature for fifteen minutes. The reaction mixture was next warmed to 25° C. and stirred for two hours. The dichloromethane was removed by evaporation under reduced pressure and the remaining solution was diluted with 39 liters of methanol and 39 liters of water. The precipitate that formed was collected by filtration and dried at 50° C. to give 3.38 kg. of diphenylmethyl 7-β-(4-methylphenylcarboxamido)-3-chloro-3-cephem-4-carboxylate.

(E) To a cold (−10° to −15° C.) stirred solution of 2.43 liters of triphenyl phosphite in 28.5 liters of methylene chloride containing 756 g. of chlorine gas and 875 ml. of pyridine were added portionwise over two hours 3.25 kg. of diphenylmethyl 7-β-(4-methylphenylcarboxamido)-3-chloro-3-cephem-4-carboxylate.

Following the addition, the reaction mixture was diluted with 434 g. of hydrogen chloride and then allowed to warm to room temperature and was stirred for two hours. The reaction mixture was then diluted with 35 liters of water, and the aqueous mixture was stirred for ten minutes. The organic layer was allowed to separate and was then removed, dried over 1 kg. of calcium chloride, and the solvent was removed by evaporation under reduced pressure. The product was crystallized from diethyl ether containing concentrated hydrochloric acid to give 1.96 kg. of 7-amino-3-chloro-3-cephem-4-carboxylic acid diphenylmethyl ester hydrochloride.

(F) The hydrochloride salt thus obtained was converted to the free base by reaction with 1500 ml. of 20% aqueous sodium carbonate solution. To a stirred cold (−45° to −50° C.) solution of 672.1 g. of 3[(α-carboxy-p-hydroxybenzyl)amino]crotonic acid methyl ester sodium salt in 10.91 liters of ethyl acetate containing 13.1 ml. of methanesulfonic acid, 13.5 ml. of N,N-dimethylbenzylamine and 181.1 ml. of methyl chloroformate was added portionwise 875 g. of diphenylmethyl 7-amino-3-chloro-3-cephem-4-carboxylate. The reaction mixture was warmed to room temperature and stirred for two hours. The reaction mixture was filtered, and the solvent was removed from the filtrate by evaporation under reduced pressure to afford a white powder. The powder was dissolved in 16.86 liters of dichloromethane and stirred while 455 g. of p-toluenesulfonic acid were added in one portion. The reaction mixture was then cooled to 0° C. and stirred while 175 ml. of ethane thiol were added, followed by the dropwise addition of 336 ml. of boron trifluoride diethyl etherate. The reaction mixture was warmed to room temperature and stirred for three hours. The mixture was then filtered and the solvent was removed by evaporation to give 608.2 g. of 7-β-[2-amino-2-(4-hydroxyphenyl)acetamido]-3-chloro-3-cephem-4-carboxylic acid, monohydrate.

EXAMPLE 20

Diphenylmethyl 7-β-phenylacetamido-7-α-methoxy-3-exomethylenecepham-1,1-dioxide-4-carboxylate To a stirred cold (0° C.) solution of 2.48 gms. (4.57 mmoles) of diphenylmethyl 7-β-phenylacetamido-7-α-methoxy-3-acetoxymethyl-3-cephem-1,1-dioxide-4-carboxylate in 50 ml of N,N-dimethylformamide and 10 ml of water were added in separate portions 2.7 gms. (20 mmoles) of zinc chloride, 4.0 gms. of ammonium chloride, and finally 5.0 gms. of activated zinc dust. The reaction mixture was stirred at 0° to 5° C. for five hours, stored at −10° C. for seventy-two hours, and then stirred for an additional three hours at 0°–5° C. The reaction mixture was then filtered and the filtrate was added to 200 ml of ethylacetate and washed twice with 200 ml portions of water and once with 200 ml of brine. The organic layer was separated, dried and concentrated to dryness to give an oil. The oil was crystallized from 25 ml of methanol to provide 530 mg (24% yield) of diphenylmethyl 7-β-phenylacetamido-7-α-methoxy-3-exomethylenecepham-1,1-dioxide-4-carboxylate. A second crop of product was crystallized from the mother liquor to give 620 mg additional product (total yield 52%).

NMR (CDCl$_3$) (on first crop of crystals): δ 3.32 (s, 3H); δ 3.65 (s, 2H); δ 3.81 (s, 2H); δ 5.1–5.5 (m, 6H); δ 6.5 (s, 1H); δ 7.33 (s, 15H).

EXAMPLE 21

Preparation of Diphenylmethyl 3-methyl-2-(2-sulfinyl-4-oxo-3-(4-methylbenzoylamino)-1-azetidinyl)-2-butenoate from a 3-exomethylene sulfone A suspension of 3.18 g (6 mmoles) of diphenylmethyl 7-β-(4-methylphenylcarboxamido)-3-exomethylenecepham-1,1-dioxide-4-carboxylate in 35 ml of N,N-dimethylformamide and 5 ml of water was stirred at 25° C. under a nitrogen blanket. Six grams of ammonium chloride were added in one portion to the reaction mixture, followed by the addition of 7.5 g of zinc metal dust that had been washed with 50 ml of 1N hydrochloride acid. The reaction mixture was stirred for twentyfour hours at 25° C., and then filtered through hyflo filter aid. The filter cake was washed with 20 ml of N,N-dimethylformamide and then with 200 ml of ethylacetate. The filtrate was washed three times with 100 ml portions of 5% (v/v) aqueous hydrochloride acid. The organic layer was separated, washed with brine, dried, and the solvent was removed by evaporation under reduced pressure to give 3.5 g of a white form identified as diphenylmethyl 3-methyl-2-(2-sulfinyl-4-oxo-3-(4-methylbenzoylamino)-1-azetidinyl)-2-butenoate.

IR (CHCl$_3$): 1778 cm$^{-1}$; NMR (CDCl$_3$): δ 2.01–2.25 (three singlets, 3H each) δ 4.70 (d, 1H); δ 5.60 (dd, 1H); δ 6.1–7.9 (m 16H; δ 9.35 (S,1H).

EXAMPLE 22

Preparation of Diphenylmethyl 3-methyl-2-(2-sodium sulfonyl-4-oxo-3-(4-methylbenzoylamino)-1-azetidinyl)-2-butenoate from a 3-exomethylene sulfone To a stirred suspension of 3.18 g (6 mmoles) of diphenylmethyl 7-β-(4-methylphenylcarboxamido)-3-exomethylenecepham-1,1-dioxide-4-carboxylate in 35 ml of N,N-dimethylprinamide and 5 ml of water were added 6.0 g of ammonium chloride followed by addition of 7.5 g of activated zinc (activated by washing twice with dilute hydrochloric acid and twice with water). The reaction mixture was stirred at 25° C. for twenty four hours under a nitrogen blanket. The reaction mixture was filtered through hyflo filter aid, and the filter cake was washed with 100 ml of ethyl acetate. The filtrate was washed with 5% aqueous hydrochloric acid and dried. The solution was stirred while a solution of 1 g (6 mm) of sodium 2-ethylhexanoate in 20 ml of ethyl acetate was added in one portion. The reaction mixture was stirred at 25° C. for sixteen hours, and then the solvent was removed by evaporation under reduced pressure to provide an oil. The oil was crystallized from 50 ml of chloroform to afford 1.0 g of diphenylmethyl 3-methyl-2-(2-sodium sulfonyl-4-oxo-3-(4-methylbenzoylamino)-1-azetidinyl)-2-butenoate of the formula

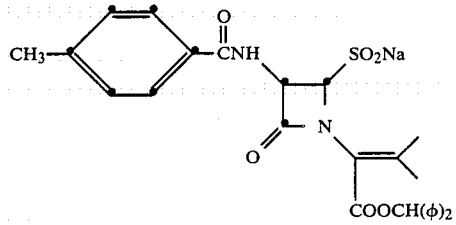

IR(KBr): 1776 am$^{-1}$; NMR(DMSod$_6$): δ 2.05 (S, 3H); δ 2.18(S, 3H); δ 2.39 (S, 3H); δ 4.56(d, 1H); δ 5.56 (dd, 1H); δ7.3–7.5 (m, 13H); δ 7.70 (d, 2H); δ 8.71 (d, 1H).

EXAMPLE 23

Preparation of diphenylmethyl α-[4-chloro-3-(4-methylphenylcarboxamido)-2-oxoazetidin-1-yl]-α-isopropylideneacetate To a stirred mixture of 1.07 g (2 m moles) of diphenylmethyl 3-methyl-2-[2-sulfinyl-4-oxo-3-(4-methylphenylcarboxamido)-1-azetidinyl)-2-butenoate (from Example 20) in 25 ml of ethyl acetate and 10 ml of saturated aqueous sodium bicarbonate were added 530 mg (4 m moles) of N-chlorosuccinimide. The reaction mixture was stirred for sixteen hours at 25° C. The organic layer was separated, washed with water and with brine, dried, and the solvent was removed by evaporation under reduced pressure to provide 900 mg of an oil. The oil was chromatographed over silica coated plates. The appropriate band was removed, washed with acetone, and the acetone was removed by evaporation to give diphenylmethyl α-[4-chloro-3-(4-methylphenylcarboxamido)-2-oxoazetidin-1-yl]-α-isopropylideneacetate.

IR(CHCl$_3$) 1780 cm$^{-1}$ β-lactam.

I claim:

1. A compound of the formula

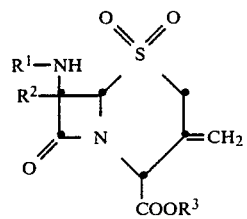

wherein:
R$^1$ is an acyl residue of a carboxylic acid;
R$^2$ is hydrogen, lower alkoxy or lower alkylthio; and
R$^3$ is a removable ester forming group.

2. The compound of claim 1 wherein R$^1$ is

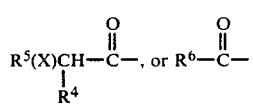

wherein:

$R^4$ is hydrogen, amino, protected amino, hydroxy, protected hydroxy, tetrazolyl, carboxy, or protected carboxy;

$R^5$ is hydrogen, phenyl, substituted phenyl, cyclohexadienyl, a 5- or 6-membered monocyclic heterocyclic ring containing one or more oxygen, sulform or nitrogen hetero atoms in the ring, said ring being substituted with hydrogen or amino;

X is oxygen or a direct link; and $R^6$ is hydrogen, phenyl, substituted phenyl, alkyl, or substituted alkyl.

3. The compound of claim 2 wherein $R^3$ is diphenylmethyl, silyl, benzyl, p-methoxybenzyl, phenacyl or tetrahydropyranyl.

4. The compound of claim 3 wherein $R^1$ is 4-methylphenylcarbonyl.

5. The compound of claim 3 wherein $R^1$ is phenoxyacetyl.

* * * * *